US012016683B2

(12) United States Patent
Steiger et al.

(10) Patent No.: US 12,016,683 B2
(45) Date of Patent: Jun. 25, 2024

(54) PORTABLE DEVICE, METHOD AND MEDICAL SYSTEM FOR PROCESSING CONTINUOUS MONITORING DATA INDICATIVE OF AN ANALYTE IN A BODILY FLUID

(71) Applicant: Roche Diabetes Care, Inc., Indianapolis, IN (US)

(72) Inventors: Bernd Steiger, Roemerberg (DE); Wilfried Schmidt, Dannstadt-Schauernheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 486 days.

(21) Appl. No.: 15/852,487

(22) Filed: Dec. 22, 2017

(65) Prior Publication Data

US 2018/0116573 A1    May 3, 2018

Related U.S. Application Data

(63) Continuation of application No. PCT/EP2016/065508, filed on Jul. 1, 2016.

(30) Foreign Application Priority Data

Jul. 1, 2015    (EP) .................... 15174910

(51) Int. Cl.
*A61B 5/145*    (2006.01)
*A61B 5/00*    (2006.01)
*A61B 5/155*    (2006.01)

(52) U.S. Cl.
CPC ........ *A61B 5/14532* (2013.01); *A61B 5/0002* (2013.01); *A61B 5/0031* (2013.01);
(Continued)

(58) Field of Classification Search
CPC . A61B 5/14532; A61B 5/0031; A61B 5/0002; A61B 5/74; A61B 5/14503; A61B 5/1427; A61M 2230/201
See application file for complete search history.

(56) References Cited

U.S. PATENT DOCUMENTS 8,579,853 B2    11/2013  Reggiardo et al.
8,849,458 B2     9/2014  Weinert et al.
(Continued)

FOREIGN PATENT DOCUMENTS

CN    102883654 A    1/2013
WO    WO 2014/070456 A1    5/2014

OTHER PUBLICATIONS

International Search Report and Written Opinion of the International Searching Authority, PCT/EP2016/065508, Aug. 29, 2016, 10 pages.
(Continued)

*Primary Examiner* — Jacqueline Cheng
*Assistant Examiner* — Tho Q Tran
(74) *Attorney, Agent, or Firm* — Bose McKinney & Evans LLP

(57) ABSTRACT

Disclosed is a portable device for processing continuous monitoring data. The portable device includes a data interface that receives a stream of continuous monitoring data from a body-worn sensor. The data is indicative of an analyte in a bodily fluid. The portable device also includes a storage device that can store the continuous monitoring data. The control processes the continuous monitoring data and is switchable between first and second modes of operation during a sensor session of the body-worn sensor. In the first mode of operation, the control is configured to provide video data indicative of the continuous monitoring data for outputting by a display. In the second mode of operation the control is configured to store the continuous monitoring data
(Continued)

in the storage device and to block the continuous monitoring data from being displayed on the display. A related method, system and computer program product are also disclosed.

11 Claims, 4 Drawing Sheets

(52) U.S. Cl.
CPC ............ *A61B 5/14503* (2013.01); *A61B 5/74* (2013.01); *A61B 5/1427* (2013.01); *A61M 2230/201* (2013.01)

(56) References Cited

U.S. PATENT DOCUMENTS

| | | | | |
|---|---|---|---|---|
| 2007/0093786 A1* | 4/2007 | Goldsmith | ......... | A61B 5/14532 604/890.1 |
| 2008/0319295 A1* | 12/2008 | Bernstein | ........... | A61B 5/14865 600/365 |
| 2009/0171170 A1* | 7/2009 | Li | ............................. | A61B 5/00 600/301 |
| 2010/0004521 A1* | 1/2010 | Epps | ....................... | H01M 8/16 600/347 |
| 2011/0022191 A1 | 1/2011 | Amit et al. | | |
| 2011/0193704 A1* | 8/2011 | Harper | ................. | A61B 5/7445 340/573.1 |
| 2012/0108934 A1* | 5/2012 | Valdes | ............... | A61B 5/14865 600/365 |
| 2012/0245447 A1* | 9/2012 | Karan | .............. | G01N 33/48792 600/365 |
| 2013/0328572 A1* | 12/2013 | Wang | ..................... | G01N 33/96 324/601 |
| 2014/0054883 A1* | 2/2014 | Lanigan | ............ | A61M 5/14248 285/33 |
| 2014/0095577 A1 | 4/2014 | Root et al. | | |
| 2014/0096264 A1* | 4/2014 | Root | ................... | A61B 5/14532 726/27 |
| 2014/0148659 A1 | 5/2014 | Sloan et al. | | |
| 2014/0180595 A1* | 6/2014 | Brumback | ............. | G16H 40/67 702/19 |
| 2014/0200426 A1 | 7/2014 | Taub et al. | | |
| 2015/0051922 A1 | 2/2015 | Rentas et al. | | |
| 2016/0262707 A1* | 9/2016 | DeVries | ................ | A61B 5/1455 |
| 2021/0366609 A1* | 11/2021 | Nabutovsky | ........... | G16H 10/20 |

OTHER PUBLICATIONS

Written Opinion of the International Preliminary Examining Authority, PCT/EP2016/065508, May 22, 2017, 6 pages.
International Preliminary Report on Patentability, PCT/EP2016/065508, Sep. 9, 2017, 35 pages.

* cited by examiner

PORTABLE DEVICE, METHOD AND MEDICAL SYSTEM FOR PROCESSING CONTINUOUS MONITORING DATA INDICATIVE OF AN ANALYTE IN A BODILY FLUID

RELATED APPLICATIONS

This application is a continuation of PCT/EP2016/065508, filed Jul. 1, 2016, which claims priority to EP 15174910.8, filed Jul. 1, 2015, both of which are hereby incorporated herein by reference in their entirety.

BACKGROUND

The present disclosure relates to a portable device and a method for processing continuous monitoring data indicative of an analyte in a bodily fluid, a medical system and a computer program product.

U.S. Publication No. 2012/0108934 A1 discloses a system for monitoring glucose concentration, which includes a continuous glucose sensor to continuously measure glucose concentration and to output a stream of continuous data associated with glucose concentration to a recording device. The device can be selectively configured to be operated in different modes of operation. A first mode of operation may be a conventional mode which may also be referred to as blinded mode, where the recording device is configured to not display data or perhaps to display only data taken from a Single point monitor, and not to provide alarm functions. In a second mode of operation, the recording device is operated as a conventional CGM system (Continuous Glucose Monitoring system). In such mode, which may also be referred to as un-blinded mode, via the display the user has access to glucose values, trend graphs, and other representations of the data being collected by the continuous glucose monitor. In a third mode of operation, the recording device restricts user access to the data being collected by the continuous analyte monitor, but still provides alarm functions to the user of the system.

Sensor data from two different analysis time periods may be compared, e.g., a first time period during which the device was in a blinded mode and a second time period during which the device was a in an un-blinded mode. A performance report is then prepared that discloses changes in sensor data over the various time periods.

U.S. Publication No. 2014/148659 A1 discloses a system related to in vivo analyte monitoring that is configurable to switch between a plurality of different operation modes or configurations. An on body electronics unit switches between different settings or uses, and the given setting can be determined by the on body unit and communicated to an analyte monitoring device. One type of use provides for the analyte monitoring device to be configured to operate in a masked mode, and a second type of use provides for the analyte monitoring device to be configured to operate in an un-masked mode. The analyte monitoring device is configured based on sensor-use information that is received from the on body unit.

SUMMARY

This disclosure teaches improved technologies for processing, in a portable device, continuous monitoring data indicative of an analyte in a bodily fluid and teaches improved flexibility of use of the portable device.

According to an aspect, a portable device for processing continuous monitoring data indicative of an analyte in a bodily fluid is provided. The portable device comprises a data interface device which is configured to receive a stream of continuous monitoring data from a body worn sensor, the continuous monitoring data being indicative of an analyte in a bodily fluid. Further, the portable device comprises a storage device which is configured to store the continuous monitoring data at least in part, and a control device which is configured to process the continuous monitoring data and, at least for data exchange, functionally connect to or communicate with the data interface device and the storage device. The control device is further configured to switch, according to a predefined operation condition, between a first and a second mode of operation during a sensor session of the body worn sensor, the first mode operation comprising providing video data indicative of the continuous monitoring data for outputting the video data by a display device, and the second mode of operation comprising storing the continuous monitoring data in the storage device and blocking displaying of the continuous monitoring data on the display device.

According to another aspect, a medical monitoring system is provided, comprising a sensor device to be worn on a body, and a portable device for processing continuous monitoring data indicative of an analyte in a bodily fluid, wherein, for at least unidirectional exchanging data, a data interface of the sensor device and a data interface of the portable device are connectable by a data transmission connection.

According to a further aspect, a method for processing continuous monitoring data indicative of an analyte in a bodily fluid in a portable device is provided. The method comprises:
controlling operation by a control device, at least for data exchange, functionally connectable to a data interface device, and a storage device,
receiving a stream of continuous monitoring data from a body worn sensor via a data interface device,
processing the continuous monitoring data in the control device, and
switching, according to a predefined operation condition, between a first and a second mode of operation during a sensor session of the body worn sensor, the first mode operation comprising providing video data indicative of the continuous monitoring data for outputting the video data by a display device, and the second mode of operation comprising storing the continuous monitoring data in the storage device at least in part and blocking displaying of the continuous monitoring data on the display device.

Another aspect refers to a computer program product, preferably stored on a storage medium and configured to perform a method for processing continuous monitoring data indicative of an analyte in a bodily fluid during operation on a portable device.

In an embodiment, the analyte to be determined may be glucose. Continuous monitoring data indicative of glucose in the bodily fluid may be provided, specifically, blood glucose.

The first mode of operation may also be referred to as an un-blinded mode of operation. The second mode of operation may also be referred to as a blinded mode of operation characterized by not displaying the continuous monitoring data on the display device, therefore, not "disclosing" the continuous monitoring data via the display device to the user of the portable device.

The blocking of displaying the continuous monitoring data on the display device may comprise blocking of providing the video data indicative of the continuous monitoring data in the portable device. As an alternative, the video data indicative of the continuous monitoring data may still be processed in the portable device, but outputting of the video data on the display is prevented. The video data processed in the portable device may be stored in a storage device of the portable device in at least one of the first and second modes of operation.

The medical monitoring system may be provided as a continuous glucose monitoring (CGM) system.

The body worn sensor may be a sensor for collecting in vivo sensor data. The body worn sensor may be a continuous monitoring sensor, specifically a continuous glucose monitoring sensor configured to be provided in the interstitium.

The sensor session of the body worn sensor may refer to a life cycle or life time of the sensor. The life cycle may be started by connecting the sensor to the portable device for the first time which may also be referred to as pairing the sensor and the portable device. The life cycle may end at the time of disconnecting the sensor from the portable device.

In the first mode of operation, displaying of the continuous monitoring data on the display device may be provided as real-time displaying.

The blinded mode of operation may be used by HCPs (Health Care Professionals) which apply continuous monitoring, e.g., CGM, for diagnostic purposes. They prefer to derive therapy adaptions based on measured patterns, e.g., glucose patterns, and profiles which are not altered by behavioral changes of the patient due to monitoring information disclosed to the user or patient. On the other hand, professional continuous monitoring systems may also be used for educational purposes allowing patients to learn more about physiological effects to nutrition, exercise, illness, insulin dosing, etc. In these cases the system is used in un-blinded mode.

The operation of the portable device in the first and second mode of operation during the sensor session may be referred to as a mixed mode of operation. It allows for a controlled switching between the blinded and un-blinded mode for one and the same sensor device during its lifetime or during a running sensor session. In particular, the HCP may set a specified time period on the portable device, such that after the specified time period the mode of operation is automatically switched to un-blinded or blinded mode. Such option for combined use, for example, allows for a single CGM-sensor to be used for both professional (blinded) and personal (un-blinded) cases. This gives the user and the HCP more flexibility and makes the CGM system more comfortable and cost-efficient. This combination of modes is particularly useful in view of CGM systems with extended sensor lifetimes, e.g., a sensor lifetime of more than 14 days.

The continuous monitoring data not displayed in the second mode of operation may be provided for a retrospective analysis, e.g., only for HCPs.

The term video data as used in the present disclosure refers to data which can be outputted over a display device.

The predefined operation condition may define one or more switching conditions. Switching between the first and second modes of operation may be performed if the switching condition(s) is fulfilled. For example, the switching condition(s) may refer to at least one of a fixed switching time, a switching date, a time period, and a period of use of the portable device after completion of which mode switching is performed. In case of having the switching condition(s) fulfilled, prior to actual switching a confirmation may be requested from the user. For example, the user may be requested to provide a confirmation input over a user interface of the portable device. Specifically, a user input may be received over a touch pad of the portable device. At the time of fulfilling the one or more switching conditions the switching may be performed automatically, i.e., without requesting any user input or user response. Specifically by automatic switching procedure, a pattern of switching events may be applied. The switching pattern is defined by the switching conditions.

A user interface device may be provided which is configured to receive a user input defining the predefined operation condition.

The control device may be configured to switch more than once between the first and the second mode of operation during the sensor session. A condition parameter for switching may be defined in response to a user input received in the portable device. The condition parameter, for example, may define a date, a time, a switching frequency, and a period of time. Switching more than once between the first and the second mode of operation may be performed over the course of several sensor sessions.

The control device may be configured to switch between the first and the second mode of operation while the stream of continuous monitoring data is received.

The control device may be configured to process a stream of continuous monitoring in vivo data.

The display device may be provided in the portable device. As an alternative, the display device may be provided separately from the portable device. For outputting the video data may be transmitted from the portable device to the separated display device via a wireless or a wired data transmission connection.

The portable device may be selected from the following group of portable devices: mobile phone, tablet computer, laptop computer, portable medical device, portable medical measurement device, and a smart watch. The portable device may be configured with a software program being downloaded from the internet, for example, in the form of a so-called App.

The control device may be configured to output a warning signal during at least one of the first and second modes of operation. The warning signal may be at least one of a visual signal and an audio signal. For example, a warning signal may be outputted if continuous glucose data processed from the continuous glucose monitoring data provide indication of a hypo- or hyperglycemia. During processing of the continuous monitoring data in the control device the warning signal may be provided for output if the continuous glucose monitoring data traverse or cross a threshold value provided in the control device. For example, a threshold for the blood glucose level may be provided. In a mode of operation, the warning signal is outputted without displaying video data indicative of the continuous glucose monitoring data traversing the threshold value (second mode of operation).

The control device may be configured to display, in the second mode of operation, further video data on the display device, such further video data being different from the video data indicative of the continuous monitoring data. The further video data may be representing event information, e.g., calendar information. The calendar information may be specifying date and/or time information. With regard to the user of the portable device, the calendar information may refer to events like insulin intake, carbohydrate intake, physical activity, and/or illness. As an alternative or in addition, the further video data may represent a result of a spot monitoring provided by a non-continuous blood glucose measurement. The portable device may be configured for non-continuous blood glucose measurement, e.g., by having a sensor device configured to analyze a test or control strip. In the portable device, the further video data and/or measurement data representing the result of the spot monitoring may be received from a measurement device, e.g., by wireless data transmission. From the measurement data received in the portable device the further video data may be derived by data processing.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
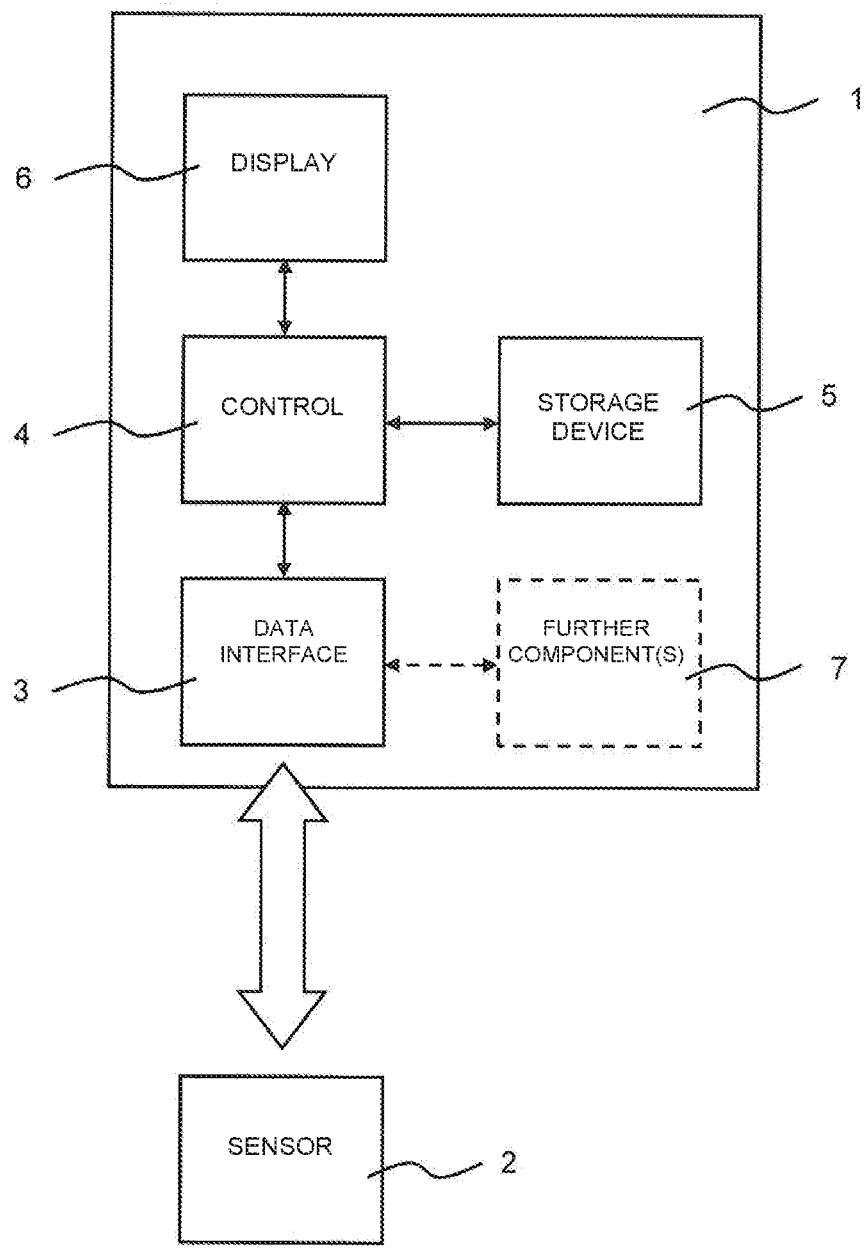
FIG. 1 is a schematic representation of an arrangement with a portable device and a sensor device to be worn on a body.

FIG. 1 shows a schematic representation of an arrangement with a portable device 1 and a sensor device or sensor 2 to be body worn by a patient. The portable device is provided with a data interface device (data interface) 3, a control device (control) 4, a storage device 5, and a display device (display) 6. As an alternative, the display device may be provided separately from the portable device 1. Video data processed in the portable device 1 may be transmitted to the separated display device for outputting. The control device 4, at least for unidirectional data transmission, is connected to the data interface device 3, the control device 4, the storage device 5, and the display device 6. Further functional components 7 may be provided.

Data transmission between the portable device 1 and the sensor device 2 may be provided by wireless and/or wired data transmission. Typically the portable device 1 receives data from the body worn sensor device 2 via a wireless connection. Preferred interfaces for such wireless communication are operable under Bluetooth or Bluetooth Low Energy Standard. On initiation of the sensor session, the portable device 1 and the body worn sensor device 2 are paired (specifically, exchange of ID information) and during the sensor session the body worn sensor device 2 may constantly transmit raw or preprocessed monitoring data to the portable device 1, where it may be either stored and displayed or only stored and not displayed.

Figure 2:
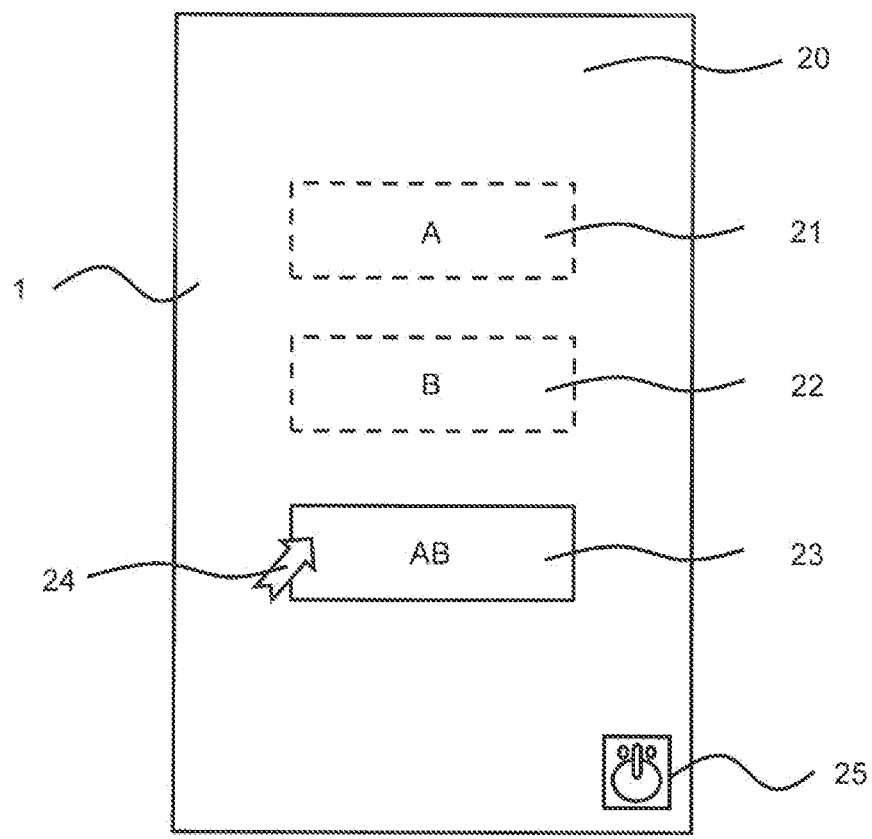
FIG. 2 is a schematic representation of a graphical output on a display device of the portable device.

FIG. 2 shows a schematic representation of a graphical output on the display device 6 of the portable device 1. A user menu 20 is shown which comprises icons 21, 22, 23 for user selection. The icons 21, 22, 23 may be selected by the user by a graphical selection element 24. Also, there is another selection area 25, which may be used by the user, for example for turning displayed pages. The icons 21, 22, 23 refer to different modes of operation of the portable device 1. Icon 21 comprising the sign "A" refers to first mode of operation in which continuous monitoring data from the body worn sensor device 2 are received by the portable device 1 and displayed on the display device 6. Such graphical outputting may be done in real time. Icon 22 comprising the sign "B" refers to a second mode of operation in which the continuous monitoring data received by the portable device 1 are stored in the storage device 5 but not displayed on the display device 6. The first and second mode of operation may be referred to as un-blinded and blinded mode of operation, respectively.

Icon 23 "AB" refers to a mode of operation (mixed mode) combining the first and second mode of operation during a sensor session.

Figure 3:
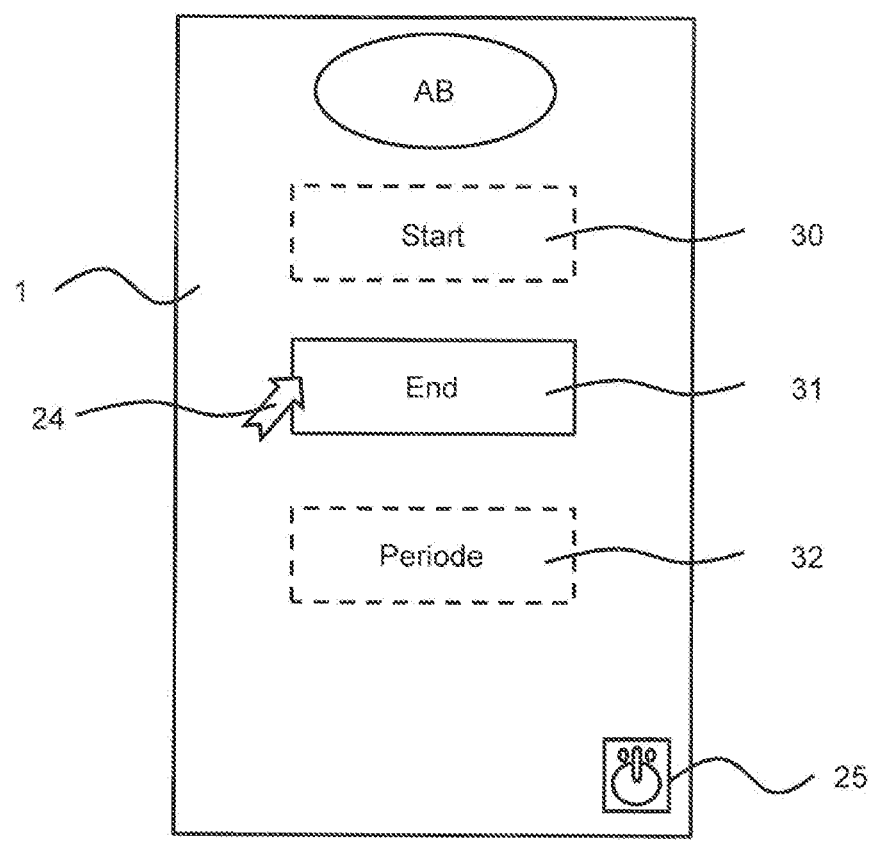
FIG. 3 is a schematic representation of another graphical output on a display device of the portable device.

If the user selects icon 23, a graphical output is presented on the graphical device 6 as shown in FIG. 3. There are several icons 30, 31, 32 providing options for defining the mixed mode of operation selected before. The user may define a starting time and an end time, and, as another option, a period of mixing the first and second mode of operation.

Figure 4:
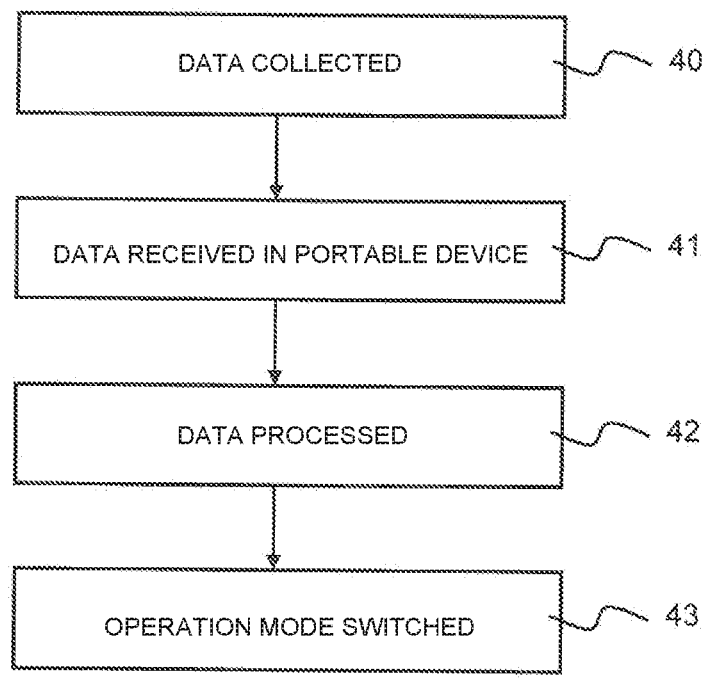
FIG. 4 is a schematic representation for a method for processing continuous monitoring data indicative of an analyte in a bodily fluid in the portable device.

FIG. 4 shows a schematic representation for a method for processing continuous monitoring data indicative of an analyte in a bodily fluid in the portable device 1. For example, glucose may be determined in the bodily fluid. In step 40, a stream of continuous monitoring data is collected by the sensor device 2. The stream of continuous monitoring data is received in the portable device 1 from the body worn sensor 2 via the data interface device 3 in step 41. In step 42, the continuous data are processed in the control device 4. During a sensor session of the body worn sensor 2 it is switched between the different modes of operation, namely the blinded and the un-blinded mode of operation (step 43).

The continuous monitoring data received in the portable device 1 may be preprocessed by the control device 4. Preprocessing data by the control device 4 may for instance include packing the data to reduce communication load and or calibrating the data according to some reference value(s), e.g., blood glucose reference value(s). Once the data is received by the portable device the processing device may process the data further. E.g., for raw data the processing may include calibration. Additionally, further data analysis such as trend analysis, threshold analysis, error analysis, and/or statistical analysis also may be performed.

The control device 4 of the portable device 1 is configured to switch between the first and second mode of operation during a running sensor session depending on a predetermined condition. Such conditions include, e.g., time, glucose thresholds for hypo- or hyperglycemia or other dangerous conditions. As mentioned before, the first mode comprises storing and not displaying the received data stream and the second mode comprises at least displaying the received data stream.

The predetermined operation condition defining the switching condition may be limited to be set through the portable device only and no distinction may be made between sensors depending on their uses. Thus, the condition may apply any time after pairing of the portable device with the sensor until the full sensor session has run.

A simple predetermined operation condition is to set a timer for, e.g., the blinded mode and switch to un-blinded mode after time has run out. Alternatively or additionally, the switching may be triggered by exceeding a threshold for a blood glucose level, i.e., if the calibrated value from the continuous monitor exceeds a threshold for hypoglycemia or hyperglycemia. This gives at least some safety net to indicate dangerous conditions to the user despite blinded mode. Further alternatively or additionally, the switching may be triggered via remote access by the HCP. In such an embodiment the data can for instance be remotely accessed by the HCP and as soon as a significant amount of data is gathered the HCP can remotely enable un-blinded mode. Such remote access may be encrypted for safety reasons.

The blinded mode includes storing and not displaying data, specifically calibrated data. However, some analysis may already be done on the not-displayed data and stored, e.g., trend analysis, threshold analysis, error analysis, statistical analysis. Also other functions such as alarm functions, warnings and/or bolus calculations may still be available to the user.

In un-blinded mode of operation the user additionally has access via the display to the glucose levels, trend graphs, and other representations of the data collected by the continuous glucose monitor. In both modes it is required to provide for reference blood glucose values for calibration purposes.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which pertains and which fall within the limits of the appended claims.

What is claimed is:

1. A portable device for processing continuous monitoring data indicative of glucose in a bodily fluid, comprising:
   a data interface configured to receive a stream of continuous monitoring data from a body-worn sensor, the continuous monitoring data being indicative of glucose in a bodily fluid;
   a storage device configured to store at least part of the continuous monitoring data; and
   a control configured to process the continuous monitoring data, the control being in communication with the data interface and the storage device, the control being pre-programmed to switch, according to a glucose threshold for hypoglycemia or hyperglycemia, between first and second modes of operation during a sensor session of the body-worn sensor;
   wherein the control is pre-programmed to switch, according to the glucose threshold for hypoglycemia or hyperglycemia, more than once between the first and second modes of operation during the sensor session;
   wherein, in the first mode of operation, the control is configured to store the continuous monitoring data in the storage device and to block video data indicative of the continuous monitoring data from being displayed on the display; and
   wherein in the second mode of operation the control is configured to provide video data indicative of the continuous monitoring data for outputting by a display.

2. Portable device according to claim 1, further comprising a user interface configured to receive a user input defining the glucose threshold for hypoglycemia or hyperglycemia.

3. Portable device according to claim 1, wherein the control is configured to switch between the first and second modes of operation while the stream of continuous monitoring data is received.

4. Portable device according to claim 1, wherein the control is configured to process a stream of continuous monitoring in vivo data.

5. Portable device according to claim 1, further comprising the display.

6. Portable device according to claim 1, wherein the control is configured to output a warning signal during at least one of the first and second modes of operation.

7. Portable device according to claim 1, wherein the control is configured in the second mode of operation to display further video data on the display, said further video data being different from the video data indicative of the continuous monitoring data.

8. A medical monitoring system, comprising:
   a sensor configured to be worn on a body; and
   a portable device, comprising:
   (i) a data interface configured to receive a stream of continuous monitoring data from the sensor, the continuous monitoring data being indicative of glucose in a bodily fluid;
   (ii) a storage device configured to store at least part of the continuous monitoring data; and
   (iii) a control configured to process the continuous monitoring data, the control being connectable to the data interface and the storage device, the control being pre-programmed to switch, according to a glucose threshold for hypoglycemia or hyperglycemia, between first and second modes of operation during a sensor session of the body-worn sensor, wherein, in the first mode of operation the control is configured to store the continuous monitoring data in the storage device and to block video data indicative of the continuous monitoring data from being displayed on the display, wherein in the second mode of operation the control is configured to provide video data indicative of the continuous monitoring data for outputting by a display, and wherein the control is pre-programmed to switch, according to the glucose threshold for hypoglycemia or hyperglycemia, more than once between the first and second modes of operation during the sensor session.

9. The medical system of claim 8, wherein the sensor has a sensor data interface and wherein the sensor data interface and the data interface of the portable device are connectable via a data transmission connection for at least unidirectional exchange of data.

10. A method for processing continuous monitoring data indicative of glucose in a bodily fluid, comprising:
   providing a portable device having a data interface, a storage device and a control;
   receiving, with the portable device, a stream of continuous monitoring data from a body worn sensor via the data interface;
   processing the continuous monitoring data in the control; and
   the control automatically switching, according to a glucose threshold for hypoglycemia or hyperglycemia between first and second modes of operation during a sensor session of the body worn sensor;
   the control automatically switching, according to the glucose threshold for hypoglycemia or hyperglycemia, more than once between the first and second modes of operation during the sensor session;
   during the first mode of operation the control storing the continuous monitoring data in the storage device and the control at least partially blocking video data indicative of the continuous monitoring data from being displayed on the display; and during the second mode of operation, providing video data indicative of the continuous monitoring data and outputting the video data to a display.

11. A non-transitory computer-readable medium having embodied thereon computer-executable instructions configured to perform the method according to claim 10 during operation on a portable device.

\* \* \* \* \*